United States Patent [19]

Parekh

[11] Patent Number: 4,742,118
[45] Date of Patent: May 3, 1988

[54] URETHANE-FUNCTIONAL S-TRIAZINE CROSSLINKING AGENTS AND CURABLE COMPOSITIONS CONTAINING THE SAME

[75] Inventor: Girish G. Parekh, Fairfield, Conn.

[73] Assignee: American Cyanamid Company, Stamford, Conn.

[21] Appl. No.: 864,622

[22] Filed: May 16, 1986

[51] Int. Cl.$^4$ .............................................. C08L 75/00
[52] U.S. Cl. .................................. 525/127; 106/176; 204/181.7; 524/589; 524/591; 525/123; 525/128; 525/424; 525/440; 525/457; 525/474; 525/528; 528/45; 528/73; 528/423; 527/301; 527/312; 544/194; 544/195; 544/196; 544/198; 544/199; 544/204; 544/209; 428/425.8
[58] Field of Search ............... 525/127, 128, 157, 424, 525/440, 474, 528, 73, 123, 457; 106/176; 528/45, 73, 423; 544/194, 195, 196, 198, 199, 204, 209; 428/425.8; 527/301

[56] References Cited

U.S. PATENT DOCUMENTS

| | | | |
|---|---|---|---|
| 3,573,301 | 3/1971 | Winter | 528/73 X |
| 4,384,102 | 5/1983 | Rasshofer et al. | 528/73 |
| 4,533,716 | 8/1985 | Okoshi et al. | 528/73 |

*Primary Examiner*—Theodore E. Pertilla
*Attorney, Agent, or Firm*—Roger S. Benjamin

[57] ABSTRACT

Novel s-triazine compounds containing at least one N,N-bis(alkoxy or hydroxyalkoxy-carbonyl-amino $C_2$–$C_{10}$ alkyl) amino substituent function in self-condensation and as crosslinkers for compounds containing active hydrogen groups. The compositions cure to coatings with excellent properties, especially corrosion resistance, humidity resistance, abrasion resistance and flexibility. The coatings have excellent exterior durability.

21 Claims, No Drawings

URETHANE-FUNCTIONAL S-TRIAZINE CROSSLINKING AGENTS AND CURABLE COMPOSITIONS CONTAINING THE SAME

The present invention relates to new and improved urethane-functional amino-s-triazine crosslinking agents, to curable compositions incorporating them and to methods of making and using the new and improved crosslinkers. More particularly, it relates to novel s-triazine compounds containing at least one N,N-bis(alkoxy- or hydroxyalkoxycarbonylamino $C_2$–$C_{10}$ alkyl)amino substituent. The novel urethane functional s-triazine crosslinking agents are useful for crosslinking active-hydrogen materials to form cured products characterized by excellent toughness, hardness and flexibility. They are especially useful for providing curable light-stable coatings for articles intended for outdoor use.

BACKGROUND OF THE INVENTION

Crosslinking agents comprising s-triazine compounds are known in the art. Koral et al., U.S. Pat. No. 3,661,819, for example, disclose a family of s-triazine curing agents comprising fully or partially alkylated melamine-formaldehyde compounds having the formula:

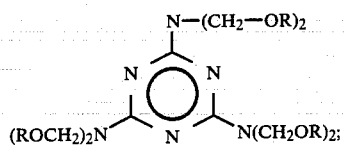

or (ii) a benzoguanamine compound of the formula:

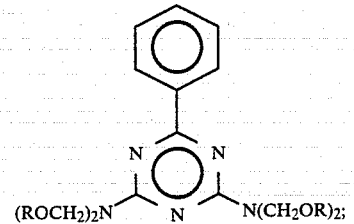

wherein R is hydrogen or alkyl of from 1 to 12 carbon atoms. It is also known to use oligomers of such compounds, which are low molecular weight condensation products containing for example two, three or four triazine rings, joined by —$CH_2OCH_2$— linkages, as well as mixtures of any of the foregoing. These are used to self-condense or used to cure active hydrogen-containing materials, especially polymers which contain carboxyl groups, alcoholic hydroxy groups, amide groups and groups convertible to such groups, such as methylol groups. Coatings containing melamine-formaldehyde crosslinkers have good hardness and high crosslink density. The coatings generally do not discolor upon exposure to light, especially ultraviolet from sunlight or other sources, moisture or oxygen. A serious shortcoming of these crosslinkers is that they tend to liberate formaldehyde on curing which is objectionable to both formulators and end-users. Moreover, coatings crosslinked with these materials have a tendency to brittleness, at least as compared with other coatings such as polyurethane coatings.

Crosslinking agents based on beta-hydroxyalkyl carbamates are known from Valko, U.S. Pat. No. 4,435,559. Valko describes curable compositions comprising a bis(beta-hydroxyalkyl carbamate) crosslinker, an active-hydrogen material and a cure catalyst. The Valko crosslinkers are prepared from diisocyanate intermediate. The coatings derived from aromatic blocked diisocyanates are not light stable in outdoor use. Although coatings prepared therefrom are more flexible than the aforementioned melamineformaldehyde based coatings, they suffer from poor crosslink density, poor hardness and poor organic solvent resistance. Moreover, they require use and handling of hazardous and toxic isocyanate materials.

Another patent dealing with beta-hydroxyalkyl carbamate crosslinkers is Jacobs, III, Parekh and Blank, U.S. Pat. No. 4,484,994, which discloses their use in cathodically electrodepositable coating compositions.

Accordingly, to overcome certain drawbacks of the prior art crosslinkers, it is an object of the present invention to provide new and improved crosslinking agents for use with active hydrogen containing materials and polymers which impart the hardness, toughness, solvent resistance and light stability of melamine-formaldehyde crosslinkers but without the brittleness, and which possess the abrasion resistance and flexibility of polyurethane coatings.

It is another object of the present invention to provide melamine-urethane crosslinkers for curable systems which are formaldehyde and isocyanate free.

It is a further object of the present invention to provide curable coating compositions for use in powder coating, electrocoating and solvent-borne coating applications.

SUMMARY OF THE INVENTION

In accordance with these and other objects, the present invention provides new and improved urethane-functional s-triazine crosslinking agents comprising:
(i) a compound of the formula

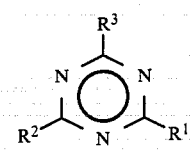

wherein $R^1$ is

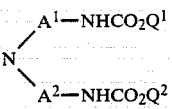

wherein $A^1$ and $A^2$ are, independently, straight or branched chain divalent alkylene of from about 2 to about 10 carbon atoms and $Q^1$ and $Q^2$ are, independently straight or branched chain alkyl or alkoxyalkyl of from about 1 to about 20 carbon atoms or straight or branched chain beta-hydroxyalkyl of from about 2 to about 10 carbon atoms; $R^2$ and $R^3$ are, independently, the same as $R^1$ and, in addition, Cl, Br, I, $OR^4$, —$NHR^5$, —$NR^5R^6$,

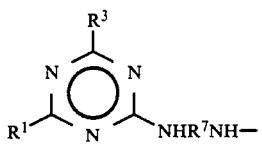

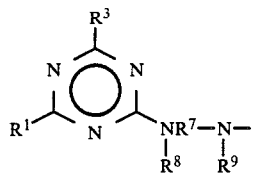

and $R^4$, $R^5$, $R^6$ are, independently, a monovalent- and $R^7$ is a divalent aliphatic, cycloaliphatic, aromatic or alkylaromatic radial, which can contain heteroatoms such as O, N, S or P, either in the chain or as side substituents and $R^8$ and $R^9$ are the same as $R^4$, $R^5$ and $R^6$ and, in addition, hydrogen or, when $R^7$, $R^8$ and $R^9$ are taken together, divalent heterocyclic incorporating the nitrogens to which they are attached;

(ii) a self-condensed oligomer of (i);

(iii) a urethane or urea compound comprising the reaction product of (i) or (ii) with a mono-or polyol or a mono- or polyamine; or (iv) a mixture of any of the foregoing.

With respect to compound (i) $A^1$ and $A^2$ are preferably $C_2$-$C_6$ alkyl and $Q^1$ and $Q^2$ are beta-hydroxyethyl, beta-hydroxy propyl, e.g., a mixture of beta-hydroxy-alpha-methylethyl and beta-hydroxy-beta-methylethyl, or a mixture of beta-hydroxypropyl and butyl or octyl. Also preferred are oligomers of (i) in which $A^1$ and $A^2$ are ethylene and $Q^1$ and $Q^2$ are beta-hydroxyethyl or beta-hydroxypropyl, as well as triazines in which $R^2$ and $R^3$ are the same as $R^1$.

Also contemplated by the present invention are thermosettable compositions comprising:

(a) a cross-linking agent comprising:

(i) a triazine compound selected from a compound of the formula:

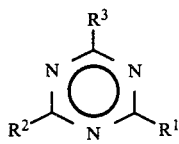

wherein $R^1$ is

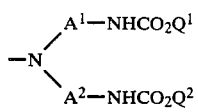

wherein $A^1$ and $A^2$ are, independently, straight or branched chain divalent alkylene of from about 2 to about 10 carbon atoms and $Q^1$ and $Q^2$ are, independently straight or branched chain alkyl or alkoxyalkyl of from about 1 to about 20 carbon atoms or straight or branched chain beta-hydroxyalkyl of from about 2 to about 10 carbon atoms; $R^2$ and $R^3$ are, independently, the same as $R^1$ and, in addition, Cl, Br, I, $OR^4$, $-NHR^5$, $-NR^5R^6$,

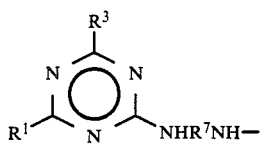

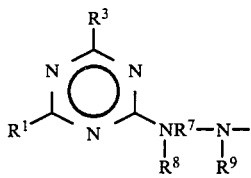

and $R^4$, $R^5$, $R^6$ are, independently, a monovalent- and $R^7$ is a divalent aliphatic, cycloaliphatic, aromatic or alkylaromatic radical, which can contain heteroatoms such as O, N, S or P, either in the chain or as side substituents and $R^8$ and $R^9$ are the same as $R^4$, $R^5$ and $R^6$ and, in addition, hydrogen or, when $R^7$, $R^8$ and $R^9$ are taken together, divalent heterocyclic incorporating the nitrogens to which they are attached;

(ii) a self-condensed oligomer of (i);

(iii) a urethane or urea compound comprising the reaction product of (i) or (ii) with a mono- or polyol or a mono- or polyamine; or (iv) a mixture of any of the foregoing, and, optionally, (b) a polymer containing two or more active hydrogen functional groups; and (c) optionally, a cross-linking catalyst; the cross-linking agent (a) and the polymer (b) being stable relative to each other in the composition at ambient temperature and reactive with each other at elevated temperature.

In preferred features of this aspect of the invention, the material (b) contains at least two reactive carboxyl, alcoholic hydroxy or amide groups, or a mixture of such groups, preferably a hydroxy-functional acrylic resin, a polyester polyol or a polyether polyol. Preferably the triazine will be as set forth specifically above, and the cure catalyst, if used, will be a metalorganic compound or quaternary salt, as set forth hereinafter.

Alternatively, the urethane-functional s-triazine compounds of the above formulae can be used as (a) a self-crosslinkable material, alone, or (b) with an optional catalyst in providing protective and/or decorative coatings and binders.

Also provided by the invention are articles of manufacture comprising substrates protectively coated with a baked and cured composition as defined above.

Also in accordance with this invention there is provided a novel process for the preparation of a triazine compound of the formula

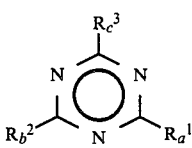

wherein $R_a^1$ is

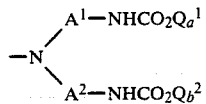

wherein $A^1$ and $A^2$ are, independently, straight or branched chain divalent alkylene of from about 2 to about 10 carbon atoms and $Q_a{}^1$ and $Q_b{}^2$ are, independently, straight or branched chain beta-hydroxyalkyl of from about 2 to about 10 carbon atoms; $R^2$ and $R^3$ are, independently, the same as $R_a{}^1$ and, in addition, Cl, Br, I or $OR_a{}^4$, wherein $R_a{}^4$ is monovalent aliphatic of from about 1 to about 6 carbon atoms, said process comprising reacting a compound of the formula

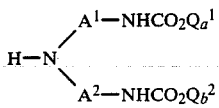

with a compound of the formula

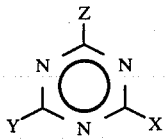

wherein at least one of X, Y and Z are displaceable groups selected from Cl, Br, I or $-OR_a{}^4$ and any remaining groups are non-displaceable groups of the formula

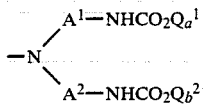

wherein $A^1$, $A^2$, $Q_a{}^1$, $Q_b{}^1$, and $R_a{}^4$ are as defined above, optionally in the presence of a condensation catalyst, until formation of the desired compound is substantially complete and, if desired, reacting a product having no more than one of said displaceable groups X, Y and Z with a dialkylamine to form a dimer, self-condensing the product to an oligomer, or forming a urethane or urea compound comprising a product from any such compound having at least one of said displaceable groups by reaction with a mono- or polyol or a mono- or polyamine, and recovering said products.

DETAILED DESCRIPTION OF THE INVENTION

As starting materials to produce the urethane-functional s-triazine crosslinking agents of this invention, there can be used the triazines, such as cyanuric chloride, and/or obvious chemical equivalents thereof known in the art. Many of the starting materials are commercially available, and they can be made by well known procedures. In accordance with the present invention, the starting materials are reacted with a bis-hydroxyalkyl iminodiethylene dicarbamate made, for example, by reacting a cyclic alkylene carbonate with a polyalkylenepolyamine, such as diethylenetriamine. The preparation of the bis-hydroxyalkyl iminodiethylene biscarbamates is described in U.S. patent application Ser. No. 581,006, filed Feb. 17, 1984 now abandoned.)

The above-cited Valko patent describes making 2-hydroxyalkyl carbamates by reacting 1,2-diols with isocyanates.

The mole ratio of beta-hydroxyalkyl carbamate to triazine compound is selected to provide the desired degree of substitution.

As will be seen by the examples herein, the reactants are mixed in suitable media, such as water-acetone-alkanol mixtures, preferably in the presence of an acid acceptor, such as sodium hydroxide, if, for example, cyanuric chloride is used as the source of the triazine ring. Low temperatures, e.g., below about 20° C. promote the formation of mono-substituted products, higher temperatures, e.g., between about 25° and 70° C. favor the formation of di-substituted products; and still higher temperatures, e.g., above about 100° C. favor tri-substitution. Recovery of the product is conventional, e.g., by precipitation and washing free of any acidic byproduct or basic acid acceptor.

The monomeric products of the process can be self-condensed to produce oligomeric compounds, suitable such compounds, e.g., monochlorotriazines can also be dimerized, e.g., by reacting with diamines, such as piperazine, and they can also be functionalized with amines, such as piperidine, as will be exemplified. Transesterification with alochols, polyols, monoamines and polyamines also produce useful derivatives, as will be shown.

The substituents defined by $A^1$, $A^2$, $Q^1$ and $Q^2$, as well as $R-R^7$ in the Formulae above can vary widely in carbon content, and the groups can be straight chain, branched chain and alicyclic. Representative compounds will be exemplified hereinafter.

Typical of radicals $A^1$ and $A^2$ are

—CH₂CH₂—

—CH₂CH₂CH₂—

—CH₂CH(CH₃)CH₂—

—CH₂CH(CH₂CH₃)(CH₂)₃)CH₂— and

—CH₂(CH₂)₈CH₂— and the like.

Illustrative of groups $Q^1$ and $Q^2$ are

—CH₃

—CH₂CH₃

—CH₂(CH₂)₁₈CH₃

—CH₂CH₂OH

—CH₂CH(CH₃)OH

—CH₂CH(OH)CH₂CH₃

—CH₂CH(OH)(CH₂)₃CH₃,

—CH₂CH(OH)(CH₂)₇CH₃, and the like.

Typical of groups $R^4$, $R^5$, $R^6$ are $C_1$–$C_{30}$ radicals such as

—CH₃

—CH₂CH₃

—CH₂(CH₂)₁₈CH₃

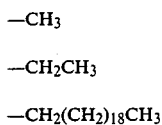

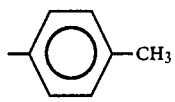

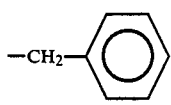

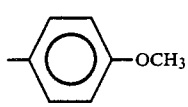

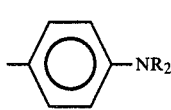

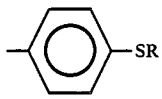

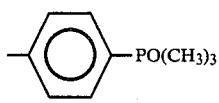

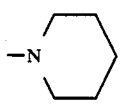

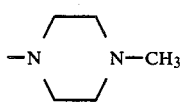

R being hydrogen or alkyl, and the like.
Typical of divalent radicals

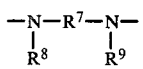

are

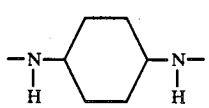

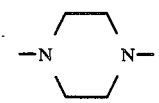

-continued
—NHCH₂CH₂NH—
—N(CH₃)CH₂CH₂N(CH₃)—
—NHCH₂CH₂NHCH₂CH₂NH—

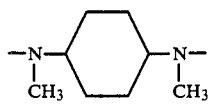

and the like.

The composition containing the crosslinking agents, polymers, and, optionally, catalyst, is heated to an elevated temperature at which the hydroxyalkyl carbamate groups of the cross-linker react with active functional groups of the polymer to cross-link the polymer and produce diol leaving groups of low toxicity, such as propylene glycol or ethylene glycol. A typical reaction sequence of, for example, a hydroxy functional group containing polymer is shown in equation (1) and that for an amine functional group containing polymer is shown in equation (2).

$$R_1\overset{H}{N}-\overset{O}{\underset{\|}{C}}-O-\overset{CH_3}{\underset{|}{C}HCH_2OH} + ROH \xrightarrow{CAT} \tag{1}$$

$$R_1\overset{H}{N}-\overset{O}{\underset{\|}{C}}O-R + HO\overset{CH_3}{\underset{|}{C}H}CH_2OH$$

$$R_1\overset{H}{N}-\overset{O}{\underset{\|}{C}}-O-\overset{CH_3}{\underset{|}{C}HCH_2OH} + RNH_2 \xrightarrow{CAT} \tag{2}$$

$$R_1\overset{H}{N}-\overset{O}{\underset{\|}{C}}-\overset{H}{N}R + HO\overset{CH_3}{\underset{|}{C}H}CH_2OH$$

With carboxyl functional group polymers, amide groups are formed in the reaction and the reaction products of the cross-linking reaction are $CO_2$ and the corresponding 1,2-diol. Generally, the leaving groups in the cross-linking reaction are, as illustrated above, diols of low toxicity, such as propylene glycol or ethylene glycol. Any attempt to prepare the above described hydroxyalkyl carbamate compounds by reaction of a diisocyanate with a di- or polyol would be difficult or impossible inasmuch as the formation of polyurethane polymers or gelation would occur.

The amount of hydroxyalkyl carbamate selected in a typical formulation will of course depend on the cross-linking density desired. Typically, the proportion and compositions of resin and cross-linker are selected to provide from about 0.2 to about 5 moles of hydroxyalkyl carbamate groups per mole of active functional group on the polymer. If larger proportions of cross-linker carbamate groups to functional sites on the polymer are used, the cross-linker will also undergo some self-condensation, as shown in equation (3).

$$RN-\overset{O}{\underset{\|}{C}}-O-\overset{R}{\underset{|}{C}HCH_2OH} \longrightarrow \tag{3}$$

$$RN-\overset{O}{\underset{\|}{C}}-O-\overset{R}{\underset{|}{C}H}-CH_2-O-\overset{O}{\underset{\|}{C}}-\overset{H}{N}-R + HO\overset{R}{\underset{|}{C}H}CH_2OH$$

The cross-linkable resins utilizable in the present invention may comprise any suitable polymer containing active hydrogen functional groups, i.e., suitable functional groups which will react, upon heating, preferably upon heating in the presence of a catalyst, with the urethane functional groups on the cross-linker of the invention. Such active groups comprise hydroxyl, amine, amide, thiol and carboxyl groups and, accordingly, resins containing such groups are utilizable in the practice of the invention. The functionality of the polymers employed can be as low as 2 but is preferably 3 or higher, and the molecular weight may range, for example, from about 300 to about 10,000. For example, acrylic polymers useful in the invention usually have a molecular weight range of from about 1,000 to about 50,000.

A typical functional group content of, for example, hydroxyl resins utilizable in the invention is from about 0.5 to about 4 milliequivalents ("meq") hydroxyl per gram of resin solids.

An illustrative, but by no means exhaustive, list of polymers which may be usefully employed in the invention includes acrylic, polyester, vinyl, epoxy, polyurethane, polyamide, cellulosic, alkyd and silicone resins. Acrylic resins useful in the invention can be derived from the acrylic acid or methacrylic acid esters of $C_1$ to $C_{18}$ aliphatic alcohols. Optionally, acrylonitrile, styrene or substituted styrene can be incorporated into the polymer. Additional comonomers suitable for such use are maleic or fumaric acid esters or half esters. Functional groups can be derived from the hydroxyalkyl esters of acrylic, methacrylic, maleic or fumaric acid. Carboxyl functionality can be derived from alpha and beta unsaturated carboxylic acids such as those mentioned below.

Polyester and alkyd resins suitable for use with the urethane-functional triazine cross-linker can be derived from diols, polyols, mono-, di-, and polybasic acids. Examples of such suitable diols or polyols are ethylene glycol, propylene glycol, 1,3-butylene glycol, diethylene glycol, dipropylene glycol, neopentyl glycol, trimethylpentane diol, cyclohexanedimethanol, trimethylolpropane, trimethylolethane and glycerine pentaerythritol. Typical carboxylic acids useful in preparing hydroxy and carboxyl functional polyester and alkyds are $C_8$ to $C_{18}$ aliphatic monocarboxylic acids, $C_4$ to $C_{10}$ aliphatic dicarboxylic acids, aromatic mono-, di, and tricarboxylic acids such as benzoic acid, o-, m-, p-phthalic acids, or tri-metallic acid, dimeric fatty acids, and hydroxy carboxylic acids such as dimethylol propionic acid or caprolactone.

Vinyl polymers particularly suitable for use in the invention are hydroxy and carboxyl functional group-containing polymers containing either vinyl chloride or vinyl acetate as one of the comonomers.

Epoxy resins particularly suitable for use in the invention are hydroxy or amine functional resins. These are normally derived from bisphenol-A, bisphenol-F, or phenol formaldehyde resins and epichlorohydrin. The epoxy resins may also be formed from cycloaliphatic epoxies.

Polyurethanes particularly suitable for use in the invention may be hydroxyl, carboxyl, or amine functional and may be derived either from polyester or polyether polyols and a polyisocyanate.

Polyamides particularly suitable for use in the invention may be either amine or carboxyl functional and can be obtained by the conventional techniques of condensing polybasic acids with polyamines or by reacting polyamines with caprolactam.

Cellulose based hydroxyl functional resins such as cellulose acetobutyrate, and hydroxyethyl cellulose can also be reacted with the hydroxyalkyl carbamate-containing amines of the invention. Hydroxy functional silicones can also be cross-linked with the hydroxyalkyl carbamate cross-linker and are therefore well-suited for use in the invention.

All of the above mentioned active functional group-containing resins can be used in either organic solvent solution, as a powdered solid, or as dispersions in water or organic co-solvent aqueous solutions. Depending on resin structure, these uncross-linked polymers will be preferably used in one of the above mentioned forms. Blends of two or more of the above polymers can also be used. Further, the polymer and carbamate cross-linking agent blend may be pigmented, as is known in the art, to achieve a desired appearance of the coating.

Depending on the application process, either a solid powder or a liquid is applied onto the substrate to be coated and after evaporation of any solvent present, the system is cured for a sufficient period of time, e.g., from several minutes to several hours, at temperatures sufficient to effect cure, e.g., from about 200° to about 400° F. (about 93° to 204° C.).

A cross-linking catalyst may be used to promote cross-linking of the thermosetting composition of the invention. The catalyst may be an external catalyst or it may be incorporated as an internal catalyst during preparation of the functional group-containing resin, as is known in the art. For example, quaternary ammonium hydroxide groups may be incorporated into the resin. Any suitable crosslinking catalyst may be utilized (such as known metal-containing catalysts, e.g., lead, tin, zinc, and titanium compounds) as well as ternary or quaternary compounds as described below. Benzyltrimethyl ammonium hydroxide, dibutyltindilaurate, tetrabutyl diacetoxy stannoxane and similar compounds are good catalysts for achieving cross-linking at elevated temperatures in the range of from about 100° to about 175° C. (about 212° to about 347° F.) for a period of a few seconds to about 30 minutes. A catalyst may be present in a formulation in the amount of from about 0.1 to about 10% by weight of the polymer, preferably from about 1 to about 5% by weight of the polymer.

The catalyst may comprise ternary or quaternary catalysts such as known compounds of the formula:

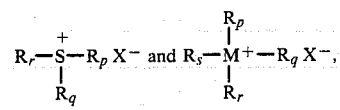

respectively, where $R_p$, $R_q$, $R_r$ and $R_s$ may be equivalent or different and may be a $C_1$ to $C_{20}$ aliphatic, aromatic, benzylic, cyclic aliphatic and the like, where M may be nitrogen, phosphorus, or arsenic (to provide, respectively, quaternary ammonium, phosphonium or arsonium compounds), where S is sulfur (to provide a ternary sulfonium compound) and where $X^-$ may be hydroxide, alkoxide, bicarbonate, carbonate, formate, acetate, lactate, and other carboxylates derived from volatile organic carboxylic acids or the like. Such salts of carboxylic acids are effective to promote the low temperature cure provided that the carboxylic acid portions of the salt are volatile.

A typical composition of the present invention contains, in weight proportions, based on the weight of resin solids for the resinous components, from about 15 to about 50 parts of the cross-linking agent of this invention, from about 50 to about 85 parts of the polymer containing two or more active hydrogen functional groups and, when present, from about 0.1 to about 5 parts of the cross-linking catalyst.

The compositions of the present invention are stable at ambient temperature and must be heated to an elevated temperature in order to cause the cross-linking reaction to occur at an appreciable rate. Generally, an elevated temperature of about 200° F. (about 93° C.) or more is required to effectuate the cross-linking reaction at an appreciable rate. As used herein and in the claims, an "elevated" temperature is one which is sufficient to cure the deposited composition by causing the cross-linking reaction to occur at a desired rate, usually a rate sufficient to effectuate cure within a period of 1 hour or less.

In many instances a pigment composition and various conventional additives such as antioxidants, surface active agents, coupling agents, flow control additives, and the like, can be included. The pigment composition may be of any conventional type, such as, one or more pigments such as iron oxides, lead oxides, strontium chromate, carbon black, titanium dioxide, talc, barium sulfate, cadmium yellow, cadmium red, chromic yellow, or the like.

After deposition on a substrate, such as a steel panel, the coating composition is devolatilized and cured at elevated temperatures by any convenient method such as in backing ovens or with banks of infrared heat lamps or in microwave ovens. Curing can be obtained at temperatures in the range of from 120° C. to about 300° C., preferably from 150° C. to about 200° C. for from about 30 minutes at the lower temperatures to about 1 minute at the higher temperatures.

DESCRIPTION OF THE PREFERRED EMBODIMENTS

The following examples illustrate the compounds and compositions of the present invention. They are not to be construed as limiting the claims in any manner. All parts are by weight.

EXAMPLE 1

2,4-Bis[N,N-bis[(2-hydroxyethoxycarbonylamino)ethyl]amino]-6-chloro-s-triazine (TECT) (I)

To 50 g water in a 3-neck flask equipped with stirrer and a thermometer, were added 9.2 g (0.05 m) of cyanuric chloride, dissolved in 50 g acetone below 10° C. To the white slurry of cyanuric chloride, 27.9 g of bis(2-hydroxyethyl)(iminodiethylene)biscarbamate (HEC), NH(CH$_2$CH$_2$NHCO$_2$CH$_2$CH$_2$OH)$_2$ dissolved in 50 g of water was added over a period of 15 minutes. During the addition, the reaction temperature was maintained below 12° C. After complete addition of HEC, the slurry turned into a clear solution. To this was added 10% caustic to maintain the reaction pH at about 7 and the reaction mixture was allowed to warm up to 25° C. At 25° C., as the reaction progressed, a white crystalline solid slowly separated out. After 4 hrs. at 25°–35° C., the solids were separated by filtration, washed with water and recrystallized from ethanol. The product yield was 24 g and m.p. 174° C. The structure of the product was confirmed by nuclear magnetic resonance (nmr) and fast atomic bombardment (fab), mass spectrometry to be that of FORMULA I:

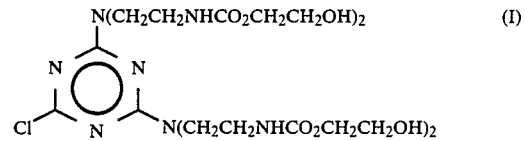

EXAMPLE 2

Hexakis[2-(2-hydroxyethoxycarbonylamino)ethyl]melamine (HECM) (II)

To 6.7 g of (I) (Example 1, TECT) were added 2.8 g HEC, 0.84 g sodium bicarbonate and 25 g ethylene glycol. The reaction mixture was then heated to 115° C. in an oil bath for 4 hours, after which most of the HEC had reacted with TECT as indicated by amine titration of the reaction mixture. Ethylene glycol was distilled off under reduced pressure. The residue was poured into methanol. Separated solids were filtered and recrystallized from methanol. Yield 5.6 g (60% of theoretical), m.p. 192° C. The nmr and fab mass spectra confirmed the product to be of FORMULA II:

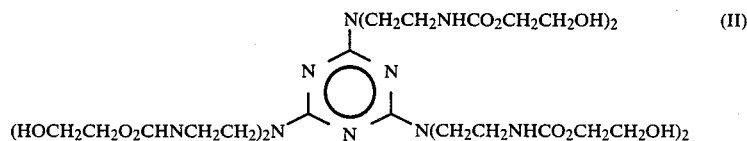

EXAMPLE 3

Hexakis[2-(2-hydroxypropoxycarbonylamino)ethyl]melamine (HPCM (III)

As in Example 1, 9.2 g (0.05 m) of cyanuric chloride was slurried into water in a suitably equipped 3 neck flask. To the slurry was added 78 g (0.02 m) of bis(2-hydroxypropyl)(iminodiethylene)bis carbamate (HPC), an isomeric mixture of NH(CH$_2$CH$_2$NHCO$_2$CH(CH$_3$)CH$_2$OH)$_2$ and NH(CH$_2$CH$_2$NHCO$_2$CH$_2$CH(CH$_3$)—OH)$_2$, (80% by weight in isobutanol) below 10° C. After complete addition of HPC to the reaction mixture, the temperature of the mixture was allowed to rise to 25° C. A clear, pale yellow solution was obtained. The clear solution after several hours at 25° C. was treated with Dowex ® 1X8 (OH$^-$) anion exchange resin to remove HCl. The HCl free solution was then stripped under reduced pressure to remove acetone and water. The water-free syrupy residue, 90 g, and 100 g of propylene glycol were heated on an oil bath to 115° C. for 4 hours. The total free amine in the mixture was 36 meq. The reaction mixture in methanol was treated first with Dowex® 1X8(OH$^-$) and subsequently with Dowex® 50WX8(H$^+$) ion exchange resins to remove Cl$^-$ and free HPC. After removal of methanol and ethylene glycol under reduced pressure a white solid product was obtained. Its structure was confirmed by spectroscopy to be of FORMULA III:

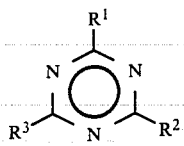

(III)

wherein $R^1$, $R^2$ and $R^3$ are $-N(CH_2CH_2NH-CO_2CH(CH_3)CH_2OH)_2$ or $-N(CH_2CH_2NH-CO_2CH_2CH(CH_3)OH)_2$ The product (III) as shown by the above formula was an isomeric mixture of compounds containing primary and secondary hydroxy groups. The yield was 32 g (64% of theory), and the melting point was 110°–120° C.

EXAMPLE 4

2,4-Bis[N,N-bis[(2-hydroxypropoxy carbonylaminoethyl]amino]-6-chloro-s-triazine (TPCT) (IV)

In a suitably equipped 3-neck flask, 9.2 g (0.05 m) of cyanuric chloride solution in 50 g of acetone was slurried in 50 g of water below 10° C. To this was added slowly 38.8 g of HPC (80% in isobutanol) dissolved in 50 g of water below 10° C., maintaining temperature of the reaction mixture. At the complete addition of HPC, the reaction mixture turned into a clear, pale yellow solution. The batch temperature was allowed to rise while maintinaing the pH of 6–7 by slow addition of 10% caustic solution to the batch. After completion of the reaction (after 3–4 hours at 25°–30° C.) water was removed from the reaction mixture by azeotroping with n-butanol under reduced pressure. The separated sodium chloride was filtered off. The clear filtrate was vacuum stripped to remove butanol. After the removal of butanol, a syrupy product was obtained, which on long standing, solidified. The mass spectrum of the syrup product indicated it to be of FORMULA IV:

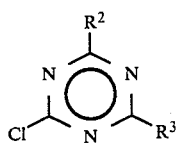

(IV)

wherein $R^2$ and $R^3$ are $-N(CH_2CH_2NHCO_2CH(CH_3)CH_2OH)_2$ or $-N(CH_2CH_2NHCO_2CH_2CH(CH_3)OH)_2$ The solidified product (TPCT), which is an isomeric mixture as shown by the above formula, was crystallized from acetone. The yield was 6 g and the melting point was 135°–140° C.

EXAMPLE 5

Reaction of FORMULA I (TECT) with Piperidine

In a suitably equipped round bottom flask were charged 6.7 g of the product of Example 1 (TECT) (0.01 m), 0.85 g (0.01 m) of piperidine and 0.84 g of sodium bicarbonate and 25 g of ethylene glycol. The mixture was heated on an oil bath to 115° C. for 4 hours. The total free base after this reaction period was 1.4 meq. Ethylene glycol was removed by distillation under reduced pressure below 150° C. The resinous product was dissolved in methanol. The separated sodium chloride was filtered off and washed with small amounts of methanol. After removal of methanol from the reaction product, a glassy solid was obtained. Mass spectra of the product indicated it to be of FORMULA V:

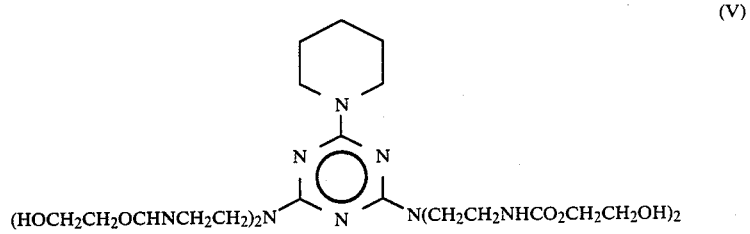

(V)

EXAMPLE 6

Reaction of FORMULA IV (TPCT) with Piperidine

In a suitably equipped round bottom flask were charged 43.5 g (0.06 m) of the product of Example 4 (TPCT), 11.5 g (0.13 m) of piperidine, 5.43 g (0.06 m) of sodium bicarbonate, and 96g of propylene glycol monomethyl ether. The mixture was heated at 120° C. for 5 hours. Sodium chloride was separated from the product by filtration. Dowex ® 50WX8(H+) ion exchange resin was added to the solution and stirred 30 minutes to remove excess amine. The resin beads were separated from the product by filtration. The propylene glycol mono-methyl ether was stripped from the product under vacuum at 110° C. The product was a resinous material. Mass spectra indicated the compound to be of FORMULA VI:

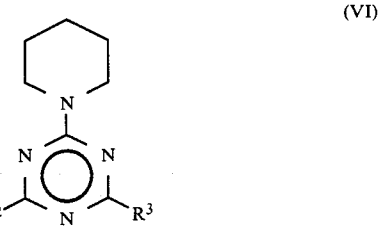

(VI)

wherein $R^2$ and $R^3$ are $-N(CH_2CH_2NHCO_2CH(CH_3)CH_2OH)_2$ or $-N(CH_2CH_2NHCO_2CH_2CH(CH_3)OH)_2$

EXAMPLE 7

Reaction of FORMULA IV (TPCT) with Dodecylamine

In a reaction vessel were charged 16.6 g (0.02 m) of the product of Example 4 (TPCT), 8.5 g (0.04 m) of dodecylamine, 1.9 g (0.02 m) of sodium bicarbonate, and 50 g of propylene glycol monomethyl ether. The mixture was heated at 115° C. for 2.5 hours. Sodium chloride was separated from the product by filtration. Dowex ® 1X8(OH—) ion exchange resin was added and the mixture was stirred 30 minutes to remove free chloride ions. The resin beads were filtered out and Dowex ® 50WX8(H+) ion exchange resin was added. The mixture was stirred 30 minutes to remove excess amine and then the resin beads were removed by filtration. The propylene glycol monomethyl ether was stripped from the product under vacuum at 110° C. The product was a resinous material. Mass spectra indicated the compound to be of FORMULA (VII):

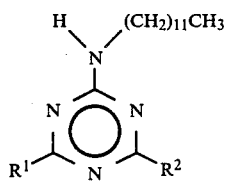

(VII)

wherein $R^1$ and $R^2$ are —N(CH$_2$CH$_2$NHCO$_2$CH(CH$_3$)CH$_2$OH)$_2$ or —N(CH$_2$CH$_2$NHCO$_2$CH$_2$CH(CH$_3$)OH)$_2$

EXAMPLE 8

Reaction of FORMULA I (TECT) with Piperazine

In a suitably equipped round bottom flask were charged 14.85 g (0.02 m) of the product of Example 1 (TECT), 0.97 g (0.01 m) of piperazine, 1.89 g (0.02 m) of sodium bicarbonate, and 53 g of propylene glycol mono-methyl ether. The mixture was heated at 115° C. for 5 hours. The propylene glycol monomethyl ether was stripped from the product under vacuum at 110° C. The solid product was washed with water to remove sodium chloride. The product was finally dried to remove water. Mass spectra indicated the product to be of FORMULA VIII:

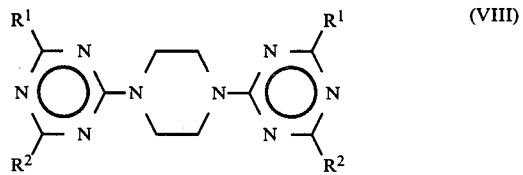

(VIII)

$R^1$ and $R^2$ are —N(CH$_2$CH$_2$NHCO$_2$CH$_2$CH$_2$OH)$_2$

EXAMPLE 9

Reaction of FORMULA IV (TPCT) with Piperazine

In a suitably equipped round bottom flask were charged 32.6 g (0.045 m) of the product of Example 4 (TPCT), 1.3 g (0.15 m) of piperazine, 3.8 g (0.045 m) of sodium bicarbonate, and 61 g of propylene glycol monomethyl ether. The mixture was heated at 115° C. for 4 hours. Sodium chloride and sodium bicarbonate were separated from the product by filtration. The propylene glycol monomethyl ether was stripped from the product under vacuum at 110° C. The product was a resinous material. Mass spectra confirmed the structure to be of FORMULA IX:

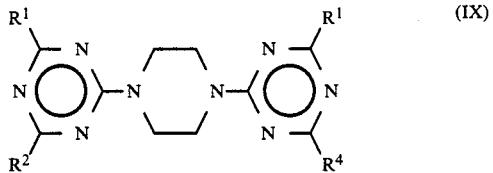

(IX)

wherein $R^1$ and $R^2$ are —N(CH$_2$CH$_2$NHCO$_2$CH(CH$_3$)CH$_2$OH)$_2$ or —N(CH$_2$CH$_2$NHCO$_2$CH$_2$CH(CH$_3$)OH)$_2$

EXAMPLE 10

Preparation of 2-Bis[N,N-bis[(2-hydroxypropoxy carbonylaminoethyl]-amino-4,6-dichloro-s-triazine (X)

To a reaction vessel is added 15.6 g (0.05 m) of bis(2-hydroxypropyl)(iminodiethylene)bis carbamate dissolved in 50 g of N-butanol. To this solution is added 4.2 g of sodium bicarbonate. Then, at 0°–5° C., is added slowly 9.2 g (0.05 m) of cyanuric chloride dissolved in 75 g of ethyl acetate. The reaction mixture is allowed to stir at 0°–5° C. and progress of the reaction was monitored by thin layer chromatography (tlc). As soon as all the cyanuric chloride is converted to monosubstituted product, the reaction mixture is filtered and washed with ethyl acetate to separate sodium chloride from the filtrate. The product is isolated by removing ethyl acetate and n-butanol under reduced pressure.

EXAMPLE 11

Preparation of 2-Bis[N,N-bis[(2-hydroxyethoxy carbonyl aminoethyl]amino]4,6-dichloro-s-triazine (XI)

This compound is prepared by the same procedure as in Example 10 except that cyanuric chloride (0.05 m) is reacted with bis(2-hydroxyethyl)(iminodiethylene)biscarbamate (0.05 m).

EXAMPLE 12

Preparation of 2,4-bis[N,N-bis[(2-hydroxypropoxy carbonyl aminoethyl]-amino]-6-di-n-butylamino-s-triazine (XII)

In a suitably equipped round bottom flask were charged 21.75 g (0.03 m) of the product of Example 4 ((TPCT), 4.65 g (0.036 m) of di-n-butylamine, 2.52 g (0.03 m) of sodium bicarbonate, and 200 g n-butanol. The mixture was heated to reflux (118°–120° C.) for 4.5 hours. The reaction was followed by thin layer chromatography (tlc). The reaction was stopped when practically all of IV was converted to the product. The reaction mixture was filtered to remove sodium chloride. The trace amount of di-n-butyl amine was removed by Dowex ® 50WX8(H+) ion exchange resin. After removal of n-butanol the product was recrystallized from ethyl acetate. Yield: 17 g (69% of theory) mp 125°–130° C. N.m.r. of the product confirmed the structure as shown below. The product is soluble in common organic solvents used in coatings.

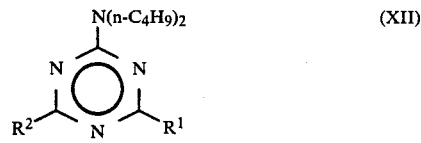

(XII)

wherein $R^1$ and $R^2$ are —N(CH$_2$CH$_2$NHCO$_2$CH$_2$(CH$_3$)CH$_2$OH$_2$)$_2$ or

—N(CH₂CH₂NHCO₂CH(CH₃)OH)₂

EXAMPLE 12

Preparation of 2,4-bis[N,N-bis[(2-hydroxypropoxy carbonyl amino ethyl]-amino]-6-di-iso-butylamino-s-triazine (XIII)

In a suitably equipped round bottom flask were charged 21.5 g (0.03 m) of the product of Example 4 (TPCT), 4.65 g (0.036 m) of diisobutylamine, 2.52 g (0.03 m) of sodium bicarbonate, and 60 g 2-propoxypropanol. The mixture was heated to reflux for 7 hours. tlc shows practically all product and only a trace amount of IV. The reaction mixture was worked up as in Example 12. After removal of solvent a sirupy product was obtained. On complete drying a glassy solid was obtained m.p. ~55° C. The yield was quantitative. The n.m.r. confirmed the structure as shown below. The product is soluble in common organic solvents such as methyl ethyl ketone, toluene, ethyl acetate, n-butanol, etc. It is insoluble in water.

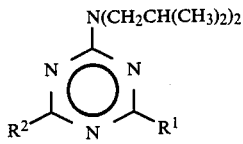

(XIII)

wherein R¹ and
R² are —N(CH₂CH₂NHCO₂CH(CH₃)CH₂OH)₂ or
—N(CH₂CH₂NHCO₂CH₂CH(CH₃)OH)₂

EXAMPLE 14

Preparation of 2-bis[N,N-bis[(2-hydroxy propoxy carbonylaminoethyl]-amino]-4,6-dibutylamino-s-triazine (XIV)

This compound is prepared in two steps. First the compound described in Example 10 is prepared without isolating it. Then, to this product 8.4 g NaHCO₃, and 12.9 g (0.1 m) of di-n-butylamine are added and the reaction temperature is raised slowly to 115° C., after distilling off ethyl acetate. The reaction temperature is maintained at 115° C. for several hours to complete the substitution of chlorine atoms by dibutylamine. After the reaction is complete, sodium chloride formed during the reaction is filtered off. After removal of n-butanol the desired product is obtained.

EXAMPLE 15

Preparation of 2-bis[N,N-bis[(2-hydroxypropoxy carbonylaminoethyl]-amino]-4,6-dianilino-s-triazine (XV)

This compound is prepared by following the procedure of Example 14, but instead of di-n-butylamine, aniline (9.2 g, 0.1 m) is used.

EXAMPLE 16

Preparation of 2-bis[N,N-bis[(2-hydroxypropoxy carbonylaminoethyl]-amino-4-butylamino-6-anilino-s-triazine (XVI)

To a suitably equipped 3-necked flask, are added 15.6 g (0.05 m) of bis(2-hydroxypropyl)(imino diethylene)bis carbamate dissolved in 50 g of n-butanol. To this solution are added slowly 9.2 g (0.05 m) of cyanuric chloride dissolved in 75 g of ethylacetate. The reaction mixture is allowed to stir at 0°–5° C. and progress of the reaction is monitored by tlc. After all the cyanuric chloride is reacted to the mono substituted product, 8.4 g of sodium bicarbonate and 3.65 g (0.05 m) of n-butylamine are added. The reaction temperature is raised to 35°–45° C. and maintained there until most of the n-butylamine has reacted. At this point 4.7 g (0.05 m) aniline are added and the reaction temperature raised to 115° C. after distilling out ethyl acetate. After about 5–6 hours, sodium chloride is filtered off. After removal of n-butanol and reaction work up the above-described product is obtained in high yields.

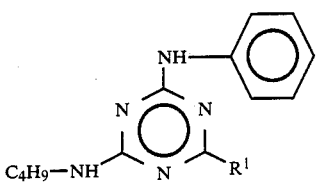

(XV)

wherein R¹ is —N(CH₂CH₂NHCO₂CH(CH₃)CH₂OH)₂ or
—N(CH₂CH₂NHCO₂CH₂CH(CH₃)OH)₂

EXAMPLE 17

Transesterification of FORMULA III to Produce Crosslinker XVII

In an autoclave were charged 100 g (0.1 m) of the compound of Example 3 (HPCM)(III), 225 g (3.0 m) of n-butanol, and 1.2 g of dibutyltindilaurate catalyst. The autoclave was heated in an oil bath on a magnetic stirrer hot plate to 155° C. The reaction mixture was kept in the oil bath at 155° C. for 5 hours. The pressure in the autoclave was about 40 psi. The resulting product mixture was a clear yellow solution. It was soluble in common organic solvents at room temperature. It was also miscible with commercially available acrylic resins and polyesters. The clear solution was concentrated to 45% solids. The proton n.m.r. of the product showed that about 40% of hydroxypropylcarbamate groups were transesterified with n-butanol. The average distribution of the hydroxypropylcarbamate to butylcarbamate was 2:3. The transesterification reaction is shown below:

—N—CH₂CH₂NHCO₂CH(CH₃)CH₂OH +

CH₃(CH₂)₂CH₂OH $\xrightarrow{\text{Tin Catalyst}}$

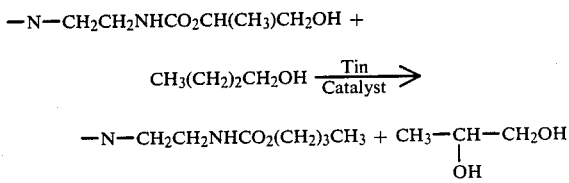

EXAMPLE 18

Preparation of Crosslinker XVIII

In an autoclave were charged 100 g (0.1 m) of the compound of Example 3 (HPCM)(III), 320 g (2.7 m) of 2-propoxypropanol, and 1.2 g of dibutyltindilaurate catalyst. The autoclave was heated in an oil bath on a magnetic stirred hot plate to 155° C. The reaction mixture in the autoclave was stirrer with a magnetic stirrer. The reaction mixture was kept in the oil bath at 155° C. for 6 hours. After this period the resulting product mixture was a pale amber solution. It was soluble in common organic solvents it was also misible with commercially available polyesters and acrylic resins such as Joncryl® 500 (S. C. Johnson and Son, Inc.). The proton n.m.r. of the product showed that about 50% of hydroxypropylcarbamate groups were transesterified with 2-propoxypropanol. The average distribution of the hydroxypropyl carbamate to 2-propoxypropyl carbamate was 1:1. The product solution was concentrated to 45.3% by partial removal of 2-propoxypropanol.

EXAMPLE 19

Self-Crosslinked Melamine-Urethane Polymer Film 2.2 g of the reaction product of piperidine and TECT (Compound V from Example 5) was dissolved in n-butanol. To this butanol solution were added 2 drops of benzyltrimethylammonium hydroxide (40%) and a drop of 1% solution of fluorocarbon surfactant FC 431 in n-butanol. The clear, pale yellow blend was cast as a film on a zinc phosphate treated cold rolled steel panel and baked at 150° C. for 20 minutes. The resulting film was very hard and glass-like, and had excellent resistance to acetone. The film thickness was 0.6 mil, Knoop hardness was 37, pencil hardness was greater than 5H and it passed the ⅛" mandrel bend test.

EXAMPLE 20

A hydroxy-functional acrylic resin was prepared by copolymerizing a blend of n-butyl acrylate (60 wt %), styrene (20 wt %), and 2-hydroxyethyl methacrylate (20 wt %), using dicumyl peroxide initiator and n-dodecyl mercaptan chain transfer agent. The polymerization was carried out in 2-ethoxyethanol at reflux temperature (135°–140° C.).

Ten grams of 75% solution of a hydroxy functional acrylic resin was blended with 2.5 g of crosslinker of FORMULA III (HPCM), 0.3 g tetrabutyl diacetoxy stannoxane catalyst and 5 g n-butanol. The blend was warmed to make it homogeneous. The well-mixed homogeneous blend was cast on a zinc phosphate treated cold rolled steel panel using #22 Wirecator®. The films were baked at 150° C. and 175° C. for 20 minutes respectively. The film properties are shown in Table 1.

TABLE 1

| Properties of Acrylic Coatings | | |
|---|---|---|
| | A | B |
| Bake schedule | 20'/150° C. | 20'/175° C. |
| Film thickness | 0.8 mil | 0.9 mil |
| Pencil hardness | 2B-B | HB-F |
| Impact resistance (Reverse) | 80 in. lbs. | 80 in. lbs. |
| MEK resistance (Double Rub) | 100+ | 100+ |
| Humidity resistance (140° F.) | Passes 2 wks. | Passes 3 wks. |

EXAMPLE 21

Four formulations were prepared by blending a commercially available polyester resin Multron® 221-75 (Mobay), crosslinker FORMULA III (HPCM) and a tin catalyst. Amounts of each component are shown in Table 2. The 175° C. baked films obtained from formulation E and F were essentially crosslinked as indicated by MEK rubs. Films from formulations C and D required 200° C. bake to achieve crosslinking. Films from formulations E and F had 200°+MEK rubs. These results show that tetrabutyl diacetoxy stannoxane (TBDAS) is a more effective catalyst than dibutyltin dilaurate (DBTL) in these formulations.

TABLE 2

| Properties of Polyester - HPCM Coatings | | | | |
|---|---|---|---|---|
| | C | D | E | F |
| Multron® 221-75 | 16 g | 15 g | 15 g | 16 g |
| Crosslinker III | 4 | 5 | 5 | 4 |
| DTL | 0.2 | 0.2 | — | — |
| TBDAS | — | — | 0.2 | 0.2 |
| n-BuOH | 8 | 8 | 8 | 8 |
| Bake Schedule | | | | |
| 175° C./20' (MEK rubs) | No cure | 35 | 175 | 100 |
| 200°/20' (MEK rubs) | 70 | 85 | 200+ | 200+ |

The results reported in Tables 1 and 2 demonstrate that the compound of FORMULA III (HPCM) functions as a cross-linker to cross-link acrylic and polyester thermoset resins with pendant hydroxy groups. The reduced cure response of the polyester resin versus that of the acrylic resin is due to the fact that the polyester resin has residual acid (acid number 10) while the acrylic resin is free of any acid (acid number 2). The presence of nonvolatile acid in the film results in retardation of cure rate of transesterification reaction required for cross-linking.

EXAMPLE 22

Modification of FORMULA III (HCPM) for Use as Cross-linker For Cathodic Electro Coating (EC) Compositions 9.96 g (0.01 m) of HPCM (Example 3) and 65 g (0.05 m) of 2-ethylhexanol were heated together to 155°–160° C. in the presence of 2 g of tetrabutyl diacetoxy stannoxane for 6½ hours. After this period, 2-ethylhexanol was distilled off under reduced pressure at 150°–160° C. A white creamy solid residue was obtained (17 g) which dissolved in n-butanol (4.7 g) to a clear amber colored solution. Mass Spectra of the product indicated the product mainly to be a mixture of the following:

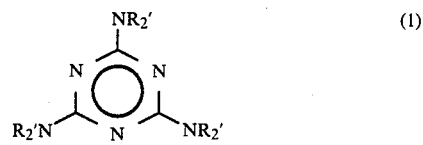

(1)

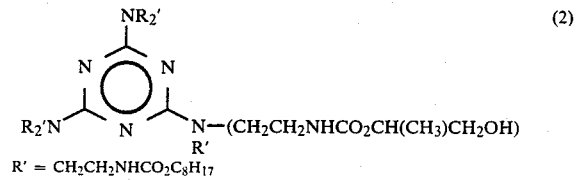

(2)

R' = CH₂CH₂NHCO₂C₈H₁₇

The product was insoluble in water and very hydrophobic. These properties make the product a suitable cross-linker for cathodic EC compositions. Similar hydrophobic cross-linkers can be prepared by oligomerization and by transesterification of FORMULA III (HPCM) with hydrophobic alcohols. Other hydrophobic s-triazine compounds with pendant hydroxyalkylcarbamate groups, carbamate groups or mixture of hydroxyalkyl carbamate groups can be used in cathodic electrocoating as crosslinking agents. The cross-linking ability of the product of this Example 22 is demonstrated in Example 23 by cross-linking a cationic resin suitable for cathodic electrocoating.

EXAMPLE 23

TABLE 4

| FORMULATION | 1 | 2* | 3 | | 4 | | 5 | | 6 | | 7 | |
|---|---|---|---|---|---|---|---|---|---|---|---|---|
| Bake Schedule °C./min. | 175 20 | 260 20 | 150 20 | 175 20 | 150 20 | 175 20 | 150 20 | 175 20 | 150 20 | 175 20 | 150 20 | 175 20 |
| Film Thickness (mils) | 0.7 | 0.6 | 1.0 | 0.7 | 0.8 | 0.8 | 0.7 | 0.6 | 0.7 | 0.5 | 1.0 | 1.0 |
| Knoop Hardness | 11.8 | — | 11.2 | 11.0 | 4.8 | 11.5 | 8.6 | 11.0 | 8.3 | 13.2 | 10.9 | 12.6 |
| Pencil Hardness | 2H | 2H | F-H | H | F | 2H | H | 2H | H | 2H | H | H |
| Humidity Resistance (140° F.) | 3 wks N.C.** | — | — | — | — | — | 3 wks N.C. | 3 wks N.C. | 3 wks N.C. | 3 wks N.C. | 3 wks 8B | 3 wks 7B |
| Salt Spray Resistance (240 hrs) | 10; 0 mm | — | — | — | — | — | 6; 3 mm | 9; 0 mm | 6; 2 mm | 9; 0 mm | 5; 10 mm | 5; 10 mm |
| MEK Double Rub | 200+ | 200+ | 200+ | 180 | 200+ | 200+ | 200+ | 200+ | 200+ | 200+ | 200+ | 200+ |
| T-Bend | | T3 passes | | | | | | | | | | |
| Impact (Rev.) in. lbs. | 0–10 | 50 | 50 | 50 | 50 | 30–40 | 50 | 50 | 50 | 50 | 0–10 | 0–10 |

*Films were cast on aluminum panels - Alodine ® 1200s
**N.C. - no corrosion

Nine and three-tenths grams of a cationic resin (prepared according to U.S. Pat. No. 3,984,299, adduct C) was blended with 6 g of the product of Example 22 (50% solution) along with 0.1 g of dibutyltin dilaurate catalyst. The blend was cast on a steel panel and baked at 175° C./20′. The film after the bake had a film thickness of 1 mil; a pencil hardness of 3H; and a MEK rub resistance of 75–100.

EXAMPLE 24

To show efficacy of crosslinking agents of FORMULAE XII, XIII, XVII, and XVIII, clear formulations were prepared using hydroxy functional acrylic and polyester resins as shown in Table 3. A formulation was also prepared with an acrylic resin and methylated melamine-formaldehyde resin, used widely in many industrial coatings (Control No. 7).

TABLE 3

Coating Formulations

| COMPOSITION | FORMULATION | | | | | | |
|---|---|---|---|---|---|---|---|
| | 1 | 2 | 3 (this invention) | 4 | 5 | 6 | 7 (control) |
| Acrylic Resin[1] | — | — | 3.6 | 7.6 | 10 | 9.3 | 57.2 |
| Joncryl ® 500[2] | 3.3 | — | — | — | — | — | — |
| Cargill 5776[3] | — | 2.9 | — | — | — | — | — |
| Crosslinker XII | — | 0.9 | — | — | — | — | — |
| Crosslinker XIII[4] 75% solution | — | — | — | — | 3.4 | 4 | — |
| Crosslinker XVII[5] | — | — | 1.65 | 4.2 | — | — | — |
| Crosslinker XVIII[6] | 1.7 | — | — | — | — | — | — |
| Cymel ® 303[7] | — | — | — | — | — | — | 12.5 |
| TBDAS[8] | 0.03 | 0.03 | 0.036 | 0.1 | 0.1 | 0.1 | — |
| n-DDBSA[9] | — | — | — | — | — | — | 0.3 |
| Resin/Crosslinker Ratio | 77/23 | 75/25 | 75/25 | 75/25 | 75/25 | 70/30 | 75/25 |

[1]Acrylic polymer prepared by copolymerizing n-butyl acrylate (50 wt %), styrene (30 wt %), and 2-hydroxy ethyl methacrylate (20%). Hydroxy No. 94, 75% solution in 2-propoxypropanol.
[2]A commercially available resin from Johnson Wax.
[3]A commercially available polyester resin from Cargill.
[4]75% solution in 2-methoxypropanol.
[5]45% solution in n-butanol.
[6]48.5% solution in 2-propoxypropanol.
[7]methylated melamine-formaldehyde resin available commercially from American Cyanamid Company (Control).
[8]Tetrabutyl diacetoxy stannoxane.
[9]n-dodecylbenzenesulfonic acid, 70% solution.

The formulations were cast on zinc phosphate pretreated steel panels and the films were baked at 150° C. and 175° C. respectively. In case of formulation 2, the films were cast on aluminium panels and baked at 260° C. for 60 seconds, commonly used in coil coating. The results of testing are set forth in Table 4:

Film properties in Table 4 show that crosslinked films obtained by utilizing crosslinking agents of FORMULAE XII, XIII, XVII and XVIII have good solvent resistance, excellent hardness, and good flexibility. The humidity and salt spray resistance of these films is also superior to the films obtained from the acrylic-methylated melamine-formaldehyde crosslinking agent based control formulation. The other advantage is that the formulations are formaldehyde free.

Experiments have also shown that, in unpigmented coatings, crosslinked films obtained by using the novel urethane-functional s-triazine crosslinker XVII had better corrosion resistance, humidity resistance and better post-forming properties as compared with films obtained with commercially available alkylated melamine formaldehyde crosslinkers as in control formulation 7.

EXAMPLE 25

TABLE 5

| | Electrodeposited Cross-linked Acrylic Coatings | | | | | |
|---|---|---|---|---|---|---|
| Deposition Voltage(v) | Time (Depositing(secs) | Bake Temp. °C. | Film Thickness (mil) | Knoop Hardness | Impact (rev.) in. lb. | MEK Rub Resistance |
| 100 | 60 | 150 | 0.62 | 11.2 | — | 200+ |
| 100 | 90 | 150 | 0.6 | 11.2 | — | 200+ |
| 100 | 90 | 175 | 0.6 | 12.0 | — | 200+ |
| 200 | 60 | 150 | 1.0 | 6.8 | 40+ | 200+ |
| 200 | 60 | 175 | 1.0 | 12.5 | 20–30 | 200+ |
| 250 | 30 | 150 | 1.0 | 6.9 | 40+ | 200+ |
| 250 | 30 | 175 | 1.0 | 12.6 | 20–30 | 200+ |

Transesterification of FORMULA III (HPCM) with 2-Butoxyethanol 50 g (0.05 m) of HPCM (III, Example 3) and 295 g of 2-butoxyethanol were heated to reflux at 160° C. in the presence of 5 g of tetrabutyl diacetoxy stannoxane for four hours. The excess 2-butoxyethanol and propylene glycol formed during the reaction were removed under reduced pressure. The viscous residue was dissolved in methanol. On standing, the tin catalyst separated from the solution. It was filtered off and an amber colored residue was dissolved in n-butanol, solids, content, 50.4%. The product was insoluble in water. The expected structure of the product having pendant 2-butoxyethylcarbamate groups is shown below. The infrared spectrum was consistent with a product of FORMULA XXV.

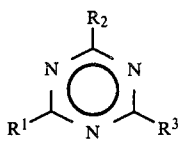

(XXV)

$R^1$ and $R^3$ are $-N(CH_2CH_2NHCO_2CH_2CH_2OC_4H_9)_2$ and $R^2$ is $-N(CH_2CH_2NHCO_2CH(CH_3)CH_2OH)_2$

EXAMPLE 26

Preparation of Cationic Acrylic Polymer and Cross-linking with Compound (XXV)

A cationic acrylic polymer with pendant hydroxy groups (Hydroxy number 90) was prepared according to U.S. Pat. No. 4,026,855 (1977), described as cationic polymeric material E in column 8. There were three minor changes (i) instead of 2-hydroxyethyl acrylate, 2-hydroxyethyl methacrylate was utilized; (ii) the monomer-acrylic acid ester of methoxy polyethylenoxyglycol (55) was eliminated; and (iii) the final resin solids were 76%. Thirty-five grams of the cationic acrylic resin, 23 g of crosslinking agent of Example 25, 12.5 g rutile titanium dioxide OR ® 600, 0.5 g acetic acid, and 0.5 g of tetrabutyl diacetoxy stannoxane were blended together on high speed stirrer to obtain good dispersion and wetting of the pigment. To this was slowly added deionized water to make up the final volume of the paint dispersion to 500 ml. The final paint solids were 10%, the bath pH was 4.9 and bath conductivity was 440 Ohm$^{-1}$ cm$^{-1}$. The bath was allowed to age overnight at room temperature. Next day phosphate coated steel panels (BO 100 ®) were electrocoated using stainless steel anode. The deposition characteristics and film properties after baking for 20 minutes are shown in Table 6.

The results in Table 6 show that the bath had good electrodeposition characteristics and films were completely crosslinked at 150° C. in 20 minutes. However, the electrocoating bath showed signs of instability after two weeks of aging at room temperature.

EXAMPLE 27

A coating composition is prepared comprising an acrylic resin which is a copolymer of n-butyl acrylate, styrene and 2-hydroxyethyl methacrylate in 2-ethoxyethanol (solids 75%, hydroxy number, 85), 18.7 g, Compound of FORMULA III (HPCM), (40% in cellosolve), 15 g, and 0.2 g of tetrabutyl diacetoxy stannoxane catalyst were blended together to form a clear resinous solution. Films were cast onto phosphate treated steel panels and baked at 150° C. for 20 minutes. The films were completely cured as indicated by resistance to 200+ MEK rubs.

EXAMPLE 28

A coating composition is prepared comprising the reaction product of 1 mole of bisphenol A and 6 moles of ethylene oxide (hydroxyl number 212, Dow Chemical Co. XD-8025 polyol), 10 g, compound of FORMULA III, (HPCM) Example 3, 6 g, tetrabutyl diacetoxy stannoxane catalyst, 0.2 g, butanol, 5 g, water 2 g, blended together until clear and homogeneous. The solution was cast onto phosphate treated steel panels and baked at 150° C. for 20 minutes. The film thickness was 0.7 mil; pencil hardness FH; Knoop hardness was 5, reverse impact resistance was 80+ in. lbs.; humidity resistance at 60° C. was 21+ days; and the MEK double rub test was 200+.

The above-mentioned patents and publications are incorporated herein by reference. Many variations of this invention will suggest themselves to those skilled in this art in light of the above, detailed description. For example, instead of hydroxyfunctional polyesters and polyacrylates, epoxy resins, such as the polyglycidylethers of bisphenol A and the reaction products thereof with amines and ammonia can be used. Or, for example, the s-triazine cross-linkers of this invention may be used in other types of coating compositions, such as high solids coatings, cathodic electrocoatings and powder coatings formulations. They may also be used in polyurethane RIM (reaction injection molding) and foam formulations as one of the polyol components. All such obvious modifications are within the full intended scope of the appended claims.

I claim:

1. A thermosettable composition comprising:
   (a) a cross-linking agent comprising:

(i) a triazine compound selected from a compound of the formula

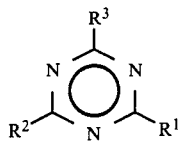

wherein $R^1$ is

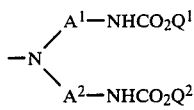

wherein $A^1$ and $A^2$ are, independently, straight or branched chain divalent alkylene of from about 2 to about 10 carbon atoms and $Q^1$ and $Q^2$ are, independently, straight or branched chain alkyl or alkoxyalkyl of from about 1 to about 20 carbon atoms or straight or branched chain beta-hydroxyalkyl of from about 2 to about 10 carbon atoms; $R^2$ and $R^3$ are, independently, the same as $R^1$ and, in addition, Cl, Br, I, $OR^4$, $-NHR^5$, $-NR^5R^6$,

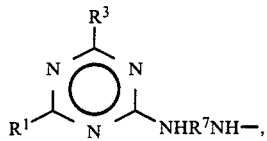

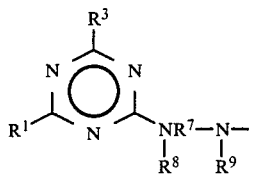

and $R^4$, $R^5$, and $R^6$ are, independently, a monovalent and $R^7$ is a divalent aliphatic, cycloaliphatic, aromatic or alkylaromatic radical, which can contain heteroatoms such as O, N, S or P, either in the chain or as side substituents and $R^8$ and $R^9$ are the same as $R^4$, $R^5$ and $R^6$ and, in addition, hydrogen or, when $R^7$, $R^8$ and $R^9$ are taken together, divalent heterocyclic incorporating the nitrogens to which they are attached;

(ii) a self-condensed oligomer of (i);
(iii) a urethane or urea compound comprising the reaction product of (i) or (ii) with a mono- or polyol or a mono- or polyamine; or
(iv) a mixture of any of the foregoing;

(b) a polymer containing two or more active hydrogen functional groups.

2. A thermosettable composition comprising:
(i) a self-condensable s-triazine compound selected from a compound of the formula:

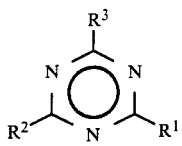

wherein $R^1$ is

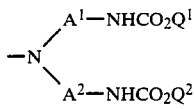

wherein $A^1$ and $A^2$ are, independently, straight or branched chain divalent alkylene of from about 2 to about 10 carbon atoms and $Q^1$ and $Q^2$ are, independently, straight or branched chain alkyl or alkoxyalkyl of from about 1 to about 20 carbon atoms or straight or branched chain beta-hydroxyalkyl of from about 2 to about 10 carbon atoms; $R^2$ and $R^3$ are, independently, the same as $R^1$ and, in addition, Cl, Br, I, $OR^4$, $-NHR^5$, $-NR^5R^6$,

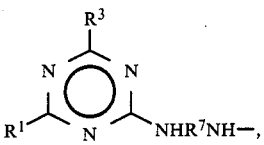

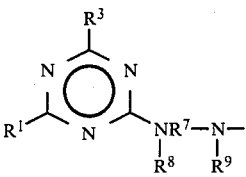

and $R^4$, $R^5$, and $R^6$ are, independently, a monovalent and $R^7$ is a divalent aliphatic, cycloaliphatic, aromatic or alkylaromatic radical, which can contain heteroatoms such as O, N, S or P, either in the chain or as side substituents and $R^8$ and $R^9$ are the same as $R^4$, $R^5$ and $R^6$ and, in addition, hydrogen or, when $R^7$, $R^8$ and $R^9$ are taken together, divalent heterocyclic incorporating the nitrogens to which they are attached;

(ii) a self-condensed oligomer of (i);
(iii) a urethane or urea compound comprising the reaction product of (i) or (ii) with a mono- or polyol or a mono- or polyamine; or
(iv) a mixture of any of the foregoing.

3. A composition as defined in claim 1 wherein the components (a)–(b) thereof are present in weight proportions, based on the weight of resin solids for the resinous components, of from about 15 to about 50 parts of the cross-linking agent (a) and from about 50 to about 85 parts of the polymer (b).

4. A composition as defined in claim 1 wherein in the triazine compound (i) $A_1$ and $A_2$ are $C_2$–$C_6$ alkylene and $Q^1$ and $Q^2$ are beta-hydroxyethyl, beta-hydroxypropyl or a $C_1$–$C_{18}$ alkyl radical.

5. A composition as defined in claim 1 wherein the molar ratio of the hydroxyalkyl carbamate groups to the active functional groups is from about 0.2 to about 5.

6. A composition as defined in claim 1 wherein said active functional groups are selected from one or more of hydroxyl groups, amino groups, amide groups, carboxyl groups or mercapto groups.

7. A composition as defined in claim 1 wherein said polymer (b) containing active functional groups is selected from the class consisting of one or more of acrylic, polyester, vinyl, epoxy, polyurethane, polyamide, cellulosic, alkyd and silicone.

8. A substrate protectively coated with a cured composition as defined in claim 1.

9. A substrate protectively coated with a cured composition as defined in claim 2.

10. A thermosettable composition comprising:
(a) a cross-linking agent comprising
  (i) a triazine compound selected from a compound of the formula

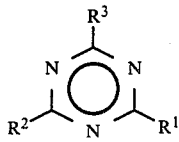

wherein $R^1$ is

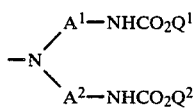

wherein $A^1$ and $A^2$ are, independently, straight or branched chain divalent alkylene of from about 2 to about 10 carbon atoms and $Q^1$ and $Q^2$ are, independently, straight or branched chain alkyl or alkoxyalkyl of from about 1 to about 20 carbon atoms or straight or branched chain beta-hydroxyalkyl of from about 2 to about 10 carbon atoms; $R^2$ and $R^3$ are, independently, the same as $R^1$ and, in addition, Cl, Br, I, $OR^4$, $-NHR^5$, $-NR^5R^6$,

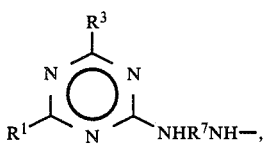

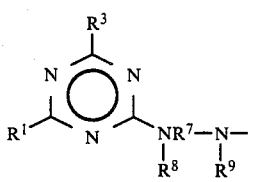

and $R^4$, $R^5$, and $R^6$ are, independently, a monovalent and $R^7$ is a divalent aliphatic, cycloaliphatic, aromatic or alkylaromatic radical, which can contain heteroatoms such as O, N, S or P, either in the chain or as side substituents and $R^8$ and $R^9$ are the same as $R^4$, $R^5$ and $R^6$ and, in addition, hydrogen or, when $R^7$, $R^8$ and $R^9$ are taken together, divalent heterocyclic incorporating the nitrogens to which they are attached;
  (ii) a self-condensed oligomer of (i);

(iii) a urethane or urea compound comprising the reaction product of (i) or (ii) with a mono- or polyol or a mono- or polyamine; or
  (iv) a mixture of any of the foregoing;
(b) a polymer containing two or more active hydrogen functional groups; and
(c) a cross-linking catalyst; the cross-linking agent (a) and the polymer (b) being stable relative to each other is the composition at ambient temperature and reactive with each other at elevated temperature.

11. A thermosettable composition comprising:
(a)
  (i) a self-condensable s-triazine compound selected from a compound of the formula:

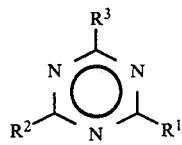

wherein $R^1$ is

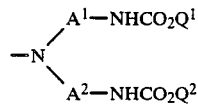

wherein $A^1$ and $A^2$ are, independently, straight or branched chain divalent alkylene of from about 2 to about 10 carbon atoms and $Q^1$ and $Q^2$ are, independently, straight or branched chain alkyl or alkoxyalkyl of from about 1 to about 20 carbon atoms or straight or branched chain beta-hydroxyalkyl of from about 2 to about 10 carbon atoms; $R^2$ and $R^3$ are, independently, the same as $R^1$ and, in addition, Cl, Br, I, $OR^4$, $-NHR^5$, $-NR^5R^6$,

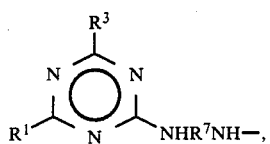

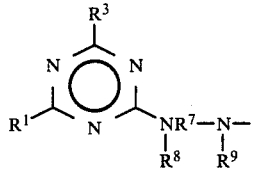

and $R^4$, $R^5$, and $R^6$ are, independently, a monovalent and $R^7$ is a divalent aliphatic, cycloaliphatic, aromatic or alkylaromatic radical, which can contain heteroatoms such as O, N, S or P, either in the chain or as side substituents and $R^8$ and $R^9$ are the same as $R^4$, $R^5$ and $R^6$ and, in addition, hydrogen or, when $R^7$, $R^8$ and $R^9$ are taken together, divalent heterocyclic incorporating the nitrogens to which they are attached;
  (ii) a self-condensed oligomer of (i);

(iii) a urethane or urea compound comprising the reaction product of (i) or (ii) with a mono- or polyol or a mono- or polyamine; or (iv) a mixture of any of the foregoing; and (b) a cross-linking catalyst.

12. A composition as defined in claim 10 wherein the components (a)–(c) thereof are present in weight proportions, based on the weight of resin solids for the resinous components, of from about 15 to about 50 parts of the cross-linking agent (a); from about 50 to about 85 parts of the polymer (b); and from about 0.1 to about 5 parts of the catalyst (c).

13. A composition as defined in claim 10 wherein in the triazine compound (i) $A_1$ and $A_2$ are $C_2$–$C_6$ alkylene and $Q^1$ and $Q^2$ are beta-hydroxyethyl, beta-hydroxypropyl or a $C_1$–$C_{18}$ alkyl radical.

14. A composition as defined in claim 10 wherein the molar ratio of the hydroxyalkyl carbamate groups to the active functional groups is from about 0.2 to about 5.

15. A composition as defined in claim 10 wherein said active functional groups are selected from one or more of hydroxyl groups, amino groups, amide groups, carboxyl groups or mercapto groups.

16. A composition as defined in claim 10 wherein said polymer (b) containing active functional groups is selected from the class consisting of one or more of acrylic, polyester, vinyl, epoxy, polyurethane, polyamide, cellulosic, alkyd and silicone resins.

17. A composition as defined in claim 10 wherein the catalyst (3) is selected from metal compound catalysts and quaternary and ternary compounds.

18. A composition as defined in claim 17 wherein the metal compound catalyst is selected from the class consisting of one or more of lead, tin, zinc, and titanium compounds.

19. A composition as defined in claim 17 wherein the catalyst is selected from the class consisting of one or more of quaternary ammonium, phosphonium, and arsonium compounds and ternary sulfonium compounds.

20. A substrate protectively coated with a cured composition as defined in claim 10.

21. A substrate protectively coated with a cured composition as defined in claim 11.

* * * * *